(12) United States Patent
Shah et al.

(10) Patent No.: US 8,216,554 B2
(45) Date of Patent: *Jul. 10, 2012

(54) STABLE TRANSFER-RESISTANT SELF-TANNING GEL CONTAINING A WATER-SOLUBLE OR WATER-DISPERSIBLE GELLING AGENT

(75) Inventors: Anil Shah, East Windsor, NJ (US); Angelike Galdi, Westfield, NJ (US); Isabelle Hansenne, Westfield, NJ (US)

(73) Assignee: L'Oreal, Paris (FR)

( * ) Notice: Subject to any disclaimer, the term of this patent is extended or adjusted under 35 U.S.C. 154(b) by 259 days.

This patent is subject to a terminal disclaimer.

(21) Appl. No.: 11/110,603

(22) Filed: Apr. 20, 2005

(65) Prior Publication Data

US 2006/0239942 A1 Oct. 26, 2006

(51) Int. Cl.
*A61K 8/00* (2006.01)
*A61K 8/18* (2006.01)
*A61Q 17/04* (2006.01)

(52) U.S. Cl. ............ 424/59; 424/401; 424/407
(58) Field of Classification Search .............. 424/401, 424/59, 407
See application file for complete search history.

(56) References Cited

U.S. PATENT DOCUMENTS

| | | | |
|---|---|---|---|
| 2,463,264 A | | 3/1949 | Graenacher et al. |
| 4,367,390 A | | 1/1983 | Balleys et al. |
| 5,166,355 A | | 11/1992 | Leistner et al. |
| 5,237,071 A | | 8/1993 | Leistner et al. |
| 5,700,452 A | * | 12/1997 | Deckner et al. .......... 424/59 |
| 6,007,826 A | * | 12/1999 | Benita et al. ............ 424/401 |
| 6,132,739 A | * | 10/2000 | Leverett ............... 424/401 |
| 6,287,543 B1 | * | 9/2001 | Terren et al. ............ 424/64 |
| 6,384,104 B1 | * | 5/2002 | Chang et al. ............ 523/105 |
| 6,613,755 B2 | | 9/2003 | Peterson et al. |
| 2004/0071641 A1 | * | 4/2004 | Boutelet et al. .......... 424/59 |
| 2004/0228814 A1 | * | 11/2004 | Candau et al. ........... 424/59 |
| 2004/0228815 A1 | * | 11/2004 | L'Alloret .............. 424/59 |
| 2005/0196364 A1 | | 9/2005 | Josso |

FOREIGN PATENT DOCUMENTS

| | | | |
|---|---|---|---|
| AU | B-51855 | * | 6/1994 |
| DE | 197 26 184 | | 12/1998 |
| DE | 197 55 649 | | 6/1999 |
| DE | 198 55 649 | | 6/2000 |
| DE | 101 62 844 | | 7/2003 |
| EP | 0 425 324 | | 5/1991 |
| EP | 0 507 691 | | 10/1992 |
| EP | 0 507 692 | | 10/1992 |
| EP | 0 517 104 | | 12/1992 |
| EP | 0 570 838 | | 11/1993 |
| EP | 0 576 189 | | 12/1993 |
| EP | 0 604 249 | | 6/1994 |
| EP | 0 669 323 | | 2/1995 |
| EP | 0 715 845 | | 6/1996 |
| EP | 0 944 624 | | 12/1996 |
| EP | 0 796 851 | | 3/1997 |
| EP | 0 971 683 | | 4/1997 |
| EP | 0 775 698 | | 5/1997 |
| EP | 0 790 243 | | 8/1997 |
| EP | 0 829 258 | | 3/1998 |
| EP | 0 832 642 | | 4/1998 |
| EP | 0 863 145 | | 9/1998 |
| EP | 0 878 469 | | 11/1998 |
| EP | 0 893 119 | | 1/1999 |
| EP | 0 903 342 | | 3/1999 |
| EP | 0 916 335 | | 5/1999 |
| EP | 0 933 376 | | 8/1999 |
| EP | 1 008 586 | | 6/2000 |
| EP | 1 013 266 | | 6/2000 |
| EP | 1 027 883 | | 8/2000 |
| EP | 1 133 980 | | 9/2001 |
| EP | 1 133 981 | | 9/2001 |
| EP | 1 300 137 | | 4/2003 |
| EP | 1 570 836 | | 9/2005 |
| FR | 2 466 492 | | 4/1981 |
| FR | 2 651 126 | | 3/1991 |
| FR | 2 816 316 | | 5/2002 |
| FR | 2 819 183 | | 7/2002 |
| FR | 2 867 070 | | 9/2005 |
| FR | 2 867 188 | | 9/2005 |
| GB | 2 303 549 | | 2/1997 |
| WO | WO-93/04665 | | 3/1993 |
| WO | WO-97/35842 | | 10/1997 |

OTHER PUBLICATIONS

Gohtani, S., Emulsion Gel and Foods, 2004, Foods Food Ingredients J. Jpn., vol. 209, No. 11.*
Pons, R., Formation and Stability of Highly Concentrated Emulsions (Gel Emulsions):Influence of Aromatic Aliphatic hydrocarbon interactions, 1997, Progr Colloid Polym Sci., 105:244-251.*
Aoki et al., "Purification and characterization of a novel β-agarase from Vibrio sp. AP-2," 187 Eur. J. Biochem. (1990) 461-65.
Lahaye & Rochas, "Chemical structure and physico-chemical properties of agar," 221 Hydrobiologia (1991) 137-48.
K. B. Guiseley in Industrial Polysaccharides: Genetic Engineering, Structure/Property Relations and Applications, vol. 3 Progress in Biotechnology (Manssur Yalpani ed.) Elsevier Science Publishing Co. Inc. NY (1987) "Natural and Synthetic Derivatives of Agarose and their use in Biochemical Separations," 139-47.

* cited by examiner

*Primary Examiner* — Rebecca Prouty
*Assistant Examiner* — Danielle Sullivan
(74) *Attorney, Agent, or Firm* — Connolly Bove Lodge & Hutz

(57) ABSTRACT

A self-tanning aqueous gel composition containing: (a) a cosmetically acceptable support; (b) at least one monocarbonyl or polycarbonyl self-tanning agent; (c) at least one aqueous phase gelling agent comprising at least one water-soluble or water-dispersible, crosslinked or non-crosslinked polymer or copolymer; d) at least one tinting agent; and (e) optionally, at least one water-soluble or water-dispersible film-forming agent.

25 Claims, No Drawings

STABLE TRANSFER-RESISTANT SELF-TANNING GEL CONTAINING A WATER-SOLUBLE OR WATER-DISPERSIBLE GELLING AGENT

BACKGROUND OF THE INVENTION

The invention relates to aqueous gels for topical use, which are intended for artificially tanning and/or browning the skin, characterized in that they comprise, in a cosmetically acceptable support, at least one monocarbonyl or polycarbonyl self-tanning agent, at least one water-soluble or water-dispersible, crosslinked or non-crosslinked polymer or copolymer and, at least one tinting agent.

The invention also relates to a cosmetic treatment process for artificially tanning and/or browning the skin, characterized in that it involves contacting the skin with an effective amount of such a composition.

It is known that monocarbonyl or polycarbonyl compounds, for instance isatin, alloxan, ninhydrin, glyceraldehyde, mesotartaric aldehyde, glutaraldehyde, erythrulose and dihydroxyacetone (DHA) are particularly advantageous products that are commonly used in cosmetics as agents for artificially tanning the skin.

When applied to the skin these compounds make it possible to obtain a tanning or brown effect that is more or less similar in appearance to that which may result from prolonged exposure to sunlight (natural tanning) or under a UV light. Such a use also has the advantage of totally avoiding the risks of cutaneous reaction generally associated with the abovementioned prolonged exposures (erythemas, burns, loss of elasticity, appearance of wrinkles, premature ageing of the skin, and the like).

Aqueous gels are particularly desired in cosmetics on account of their provision of water, which gives a pleasant sensation of freshness to the skin and due to the fact that they do not have a greasy feel. One problem associated with the use of aqueous self-tanning compositions, particularly those which are already tinted, is their tendency to stain clothes during, and/or after, application onto a user's skin.

Yet another problem associated with the use of aqueous self-tanning compositions, especially those based on polycarbonyl compounds such as dihydroxyacetone (DHA), is their lack of storage stability. For example, the stability of an aqueous self-tanning composition containing DHA typically drops approximately 30 to 40% over a period of eight weeks.

Another problem addressed by the present invention relates to the tendency of tanning composition to peel and/or pill on a user's skin during application of the composition. The friction resulting from rubbing the tanning composition onto the skin oftentimes results in the composition peeling and/or pilling on the skin.

There is thus a need to find a novel self-tanning composition based on a monocarbonyl or polycarbonyl compound in the form of an aqueous gel, which does not have the drawbacks defined above and which has good cosmetic properties, i.e., non-runny feel, non-peeling/pilling, fresh effect and good self-tanning efficacy on the skin (intensity and staying power for the coloration).

Thus, after considerable research conducted in this matter, the Applicant has now found, entirely surprisingly and unexpectedly, that it is possible to achieve these objectives by using a gelling agent comprised of at least one water-soluble or water-dispersible, crosslinked or non-crosslinked polymer or copolymer.

SUMMARY OF THE INVENTION

The invention thus relates to a self-tanning aqueous gel containing, in a cosmetically acceptable support, at least one monocarbonyl or polycarbonyl self-tanning agent, an aqueous-phase gelling agent comprised of at least one water-soluble or water-dispersible, crosslinked or non-crosslinked polymer or copolymer, at least one tinting agent used for tinting the aqueous self-tanning composition and, optionally, at least one water-soluble or water-dispersible film-forming agent.

For the purposes of the present invention, the expression "artificial colouring of the skin" will be intended to mean a non-covering (non-opacifying) and long-lasting coloration that does not come off either with water or using a solvent, and which is resistant both to friction and to washing with a solution containing surfactants. Such a long-lasting, non-covering coloration is thus distinguished from the covering and temporary coloration provided, for example, by a makeup product.

The present invention is also directed to a process for making a transfer resistant and stable self-tanning aqueous gel composition involving the steps of:
a) providing cosmetically acceptable support;
b) providing at least one monocarbonyl or polycarbonyl self-tanning agent;
c) providing an aqueous-phase gelling agent comprised of at least one water-soluble or water-dispersible, crosslinked or non-crosslinked polymer or copolymer;
d) optionally, providing at least one tinting agent;
e) optionally, providing at least one water-soluble or water-dispersible film-forming agent; and
f) combining (a)-(e) to form the transfer resistant and stable self-tanning aqueous gel composition.

The invention also relates to a cosmetic treatment process for artificially tanning and/or browning the skin in a transfer resistant manner involving contacting the skin with an effective amount of the above-disclosed aqueous gel composition.

DETAILED DESCRIPTION

Other than in the operating examples, or where otherwise indicated, all numbers expressing quantities of ingredients and/or reaction conditions are to be understood as being modified in all instances by the term "about".

The term "aqueous gel" means a composition containing a continuous aqueous phase containing a viscoelastic mass formed from colloidal suspensions. The viscosity of a gel according to the invention is measured at 25° C. using a Rheomat RM180 machine (rotor 2 or 3) from the company Rheometric Scientific, and its value is generally at least 60 DU (Deviation Units) with the rotor 2.

The gels in accordance with the present invention comprise an aqueous phase generally in a proportion of greater than or equal to 70% by weight, preferably greater than or equal to 80% by weight and more particularly greater than or equal to 90% by weight relative to the total weight of the gel.

The term "aqueous phase gelling agent" means an ingredient which is capable of gelling the aqueous phase of the invention. In order to be an adequate aqueous phase gelling agent, the ingredient is should be water-soluble or water-dispersible, and may be either nonionic or anionic in character. A variety of gelling agents are suitable for gelling the aqueous phase, including polysaccharides, PPC's, acrylic polymers, and the like.

Polysaccharides are suitable aqueous phase gelling agents. Examples of polysaccharides include galactans, galactomannans, glucomannans, polyuronic acids, and the like. Preferably the polysaccharides exhibit pendant hydrophilic groups, which are preferably sulfate. Suitable galactans are agar, agarose, kappa carageenan, iota carageenan, lambda carageenan, and the like. Examples of suitable galactomannans are locust bean gum and guar; examples of glucans are cellulose, starch, dextrans, pullulan, beta 1,3-glucans, chitin, xanthan, tamarind and the like; examples of glucomannans are konjac; examples of polyuronic acids are algin, alginates, pectins; examples of heteropolysaccharides are gellan, welan, gum arabic, karaya gum, okra gum, aloe gum, gum tragacanth, gum ghatti quinceseed gum, psyllium, starch arabinogalactan and so on. Also suitable are dextran sulfate, heparin, pectin, sodium alginate, cellulose gum, cellulose acetate priopionate carboxylate, hydroxyethyl cellulose, hydroxypropyl cellulose, and the like, and mixtures thereof. The polysaccharides may be derivatized with various groups such as sulfate, carboxylate, hydroxyl, and so on, provided the resulting polysaccharide still retains water solubility, or at the very least water dispersibility.

Preferred are galactans, particularly galactans where the pendant hydrophilic groups are sulfate groups. Most preferred is agar and carageenan, which are anionic polysaccharides comprised of basic repeating units of 1,3-linked beta-D-galactopyranose and 1,4-linked 3,6-anhydro-alpha-L-galactopyranose saccharide moieties and having pendant sulfate groups. These galactans may be further modified as taught in Aoki, T. T.; Araki & M. Kitamikado; 1990, Vibrio sp. AP-2. Eur. J. Biochem, 187, 461-465, which is hereby incorporated by reference, provided it contains the requisite number of hydrophilic pendant groups. The average molecular weight of agar ranges between 35,700 and 144,000 daltons. The galactans suitable for use in the compositions of the invention may be from any suitable source or locale. For example an article authored by M. Lahaye and C. Rochas, Hydrobiologia, 221, 137-148, 1991, which is hereby incorporated by reference, discusses the numerous different types of galactans from different origins of seaweed species, all of which are suitable for use in the compositions of the invention. Also suitable for use in the compositions of the invention are chemically modified galactans, such as those taught in an article authored by K. B. Guiseley in Industrial Polysaccharides: Genetic Engineering. Structure/Property Relations and Applications, Edited by M. Yalpani, 1987, Elsevier Science Publishers, which is hereby incorporated by reference. The Guiseley article teaches methods for the chemical modification of agar to obtain optimum gelling properties. In general, any modification of the galactans which does not affect the helical conformation (i.e. which is obtained via linkage of the O6 and O4 of galactose to the O2 of 3,6-anhydrogalactose) will preserve the gelling capability and is suitable for use in the compositions of the invention provided the requisite number of hydrophilic groups are present. The hydrophilic groups provide a polysaccharide which is water soluble.

Also suitable as aqueous phase gelling agents are anionic polymers, such as acrylic polymers which are generally sold in the form of aqueous solutions or dispersions. Such acrylic polymers may be homo- or copolymers of monomers such as acrylamide, methacrylamide, acrylic acid, methacrylic acid, $C_{1-22}$ alkyl acrylates, $C_{1-22}$ alkyl methacrylates, and so on. The monomers may also be copolymerized with other organic compounds such as alkoxylated fatty alcohols. The resulting polymers may also be cross-linked with cross-linking agents such as the allyl ether of sucrose, pentaerythritol, or propylene.

Preferred are copolymers of monomers A or B, wherein A is selected from the group consisting of acrylic acid, methacrylic acid, and mixtures thereof; and B is selected from the group consisting of a $C_{1-22}$ alkyl acrylate, a $C_{1-22}$ alkyl methacrylate, and mixtures thereof. Preferably, the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. Most preferably, the acrylic copolymer is supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. One example of such an acrylic polymer solution is sold by Seppic, Inc., under the tradename Capigel, in particular, Capigel 98, which is a white liquid having a pH of 2 to 4, a solids content of about 29-31, a density of 1.04 to 1.08, and a viscosity of 700-1000 millipascal seconds at 25° C.

Other types of polymers may contain A and B monomers which are copolymerized with alkoxylated fatty alcohols having the general formula:

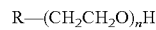

wherein n is 1-500.

Examples of polymers containing A and B monomers polymerized with alkoxylated alcohols include acrylates/steareth-50 acrylate copolymer, acrylates/steareth-20 methacrylate copolymer, and the like. Such polymers are sold under the tradenames Acrysol and Acculyn by Rohm & Haas, and Antil by Goldschmidt.

Also suitable are homo- or copolymers of monomers A and B above, which are cross-linked with various cross-linking agents such as the allyl ether of sucrose, the allyl ether of pentaerythritol, or the allyl ether of propylene. Examples of these polymers include those sold under the CTFA name Carbomer, which is defined as a homopolymer of acrylic acid crosslinked with an allyl ether of sucrose, pentaerythritol, or propylene. Carbomers are sold under the tradename Carbopol by B. F. Goodrich or Tego by Goldschmidt, as well as other vendors.

An especially preferred aqueous phase gelling agent for use in the present invention is a water-soluble or water-dispersible polymer based on crosslinked or non-crosslinked homopolymers or copolymers comprising at least the acrylamido-2-methylpropanesulfonic acid (AMPS) monomer, in a form partially or totally neutralized with a mineral base other than ammonia, such as sodium hydroxide or potassium hydroxide.

They are preferably totally neutralized or virtually totally neutralized, i.e. at least 90% neutralized.

These AMPS polymers according to the invention may be crosslinked or non-crosslinked.

When the polymers are crosslinked, the crosslinking agents may be chosen from the polyolefinically unsaturated compounds commonly used for the crosslinking of polymers obtained by free-radical polymerization.

Examples of crosslinking agents that may be mentioned include divinylbenzene, diallyl ether, dipropylene glycol diallyl ether, polyglycol diallyl ethers, triethylene glycol divinyl ether, hydroquinone diallyl ether, ethylene glycol or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allylic or vinyl ethers of polyfunctional alcohols, and also allylic esters of phosphoric and/or vinylphosphonic acid derivatives, or mixtures of these compounds.

According to one embodiment of the invention, the crosslinking agent is chosen from methylenebis-acrylamide, allyl methacrylate and trimethylolpropane triacrylate (TMPTA). The degree of crosslinking generally ranges from 0.01 mol % to 10 mol % and more particularly from 0.2 mol % to 2 mol % relative to the polymer.

The AMPS polymers in accordance with the invention are water-soluble or water-dispersible. In this case they are:
either "homopolymers" comprising only AMPS monomers and, if they are crosslinked, one or more crosslinking agents such as those defined above;
or copolymers obtained from AMPS and from one or more hydrophilic or hydrophobic ethylenically unsaturated monomers and, if they are crosslinked, one or more crosslinking agents such as those defined above. When the said copolymers comprise hydrophobic ethylenically unsaturated monomers, these monomers do not comprise a fatty chain and are preferably present in small amounts.

For the purposes of the present invention, the term "fatty chain" means any hydrocarbon-based chain containing at least 7 carbon atoms.

The term "water-soluble or water-dispersible" means polymers which, when introduced into an aqueous phase at 25° C., to a mass concentration equal to 1%, make it possible to obtain a macroscopically homogeneous and transparent solution, i.e. a solution that has a maximum light transmittance value, at a wavelength equal to 500 nm, through a sample 1 cm thick, of at least 60% and preferably of at least 70%.

The "homopolymers" according to the invention are preferably crosslinked and neutralized, and they may be obtained according to the preparation process comprising the following steps:
(a) the monomer such as AMPS in free form is dispersed or dissolved in a solution of tert-butanol or of water and tert-butanol;
(b) the solution or dispersion of monomer obtained in (a) is neutralized with one or more mineral or organic bases, preferably ammonia $NH_3$, in an amount making it possible to obtain a degree of neutralization of the sulfonic acid functions of the polymer ranging from 90% to 100%;
(c) the crosslinking monomer(s) is(are) added to the solution or dispersion obtained in (b);
(d) a standard free-radical polymerization is performed in the presence of free-radical initiators at a temperature ranging from 10 to 150° C.; the polymer precipitates in the solution or dispersion based on tert-butanol.

The water-soluble or water-dispersible AMPS copolymers according to the invention contain water-soluble ethylenically unsaturated monomers, hydrophobic monomers or mixtures thereof.

The water-soluble comonomers may be ionic or nonionic.

Among the ionic water-soluble comonomers, examples that may be mentioned include the following compounds and the salts thereof:
(meth)acrylic acid,
styrenesulfonic acid,
vinylsulfonic acid and (meth)allylsulfonic acid,
vinylphosphonic acid,
maleic acid,
itaconic acid,
crotonic acid,
the water-soluble vinyl monomers of formula (A) below:

in which:
$R_1$ is chosen from H, $-CH_3$, $-C_2H_5$ and $-C_3H_7$
$X_1$ is chosen from:
alkyl ethers of $-OR_2$ type in which $R_2$ is a linear or branched, saturated or unsaturated hydrocarbon-based radical containing from 1 to 6 carbon atoms, substituted with at least one sulfonic ($-SO_3-$) and/or sulfate ($-SO_4-$) and/or phosphate ($-PO_4H_2-$) group.

Among the nonionic water-soluble comonomers, examples that may be mentioned include:
(meth)acrylamide,
N-vinylacetamide and N-methyl-N-vinylacetamide,
N-vinylformamide and N-methyl-N-vinylformamide,
maleic anhydride,
vinylamine,
N-vinyllactams comprising a cyclic alkyl group containing 4 to 9 carbon atoms, such as n-vinylpyrrolidone, N-butyrolactam and N-vinylcaprolactam,
vinyl alcohol of formula $CH_2=CHOH$,
the water-soluble vinyl monomers of formula (B) below:

in which:
$R_{15}$ is chosen from H, $-CH_3$, $-C_2H_5$ and $-C_3H_7$
$X_2$ is chosen from:
alkyl ethers of $-OR_{16}$ type in which $R_{16}$ is a linear or branched, saturated or unsaturated hydrocarbon-based radical containing from 1 to 6 carbons, optionally substituted with a halogen atom (iodine, bromine, chlorine or fluorine); a hydroxyl group ($-OH$); ether.

Mention is made, for example, of glycidyl (meth)acrylate, hydroxyethyl methacrylate and (meth)acrylates of ethylene glycol, of diethylene glycol or of polyalkylene glycol.

Among the fatty-chain-free hydrophobic comonomers, examples that may be mentioned include:
styrene and its derivatives, such as 4-butylstyrene, α-methylstyrene and vinyltoluene,
vinyl acetate of formula $CH_2=CH-OCOCH_3$;
vinyl ethers of formula $CH_2=CHOR$ in which R is a linear or branched, saturated or unsaturated hydrocarbon-based radical containing from 1 to 6 carbons;
acrylonitrile,
caprolactone,
vinyl chloride and vinylidene chloride, silicone derivatives, which lead to silicone polymers after polymerization, such as methacryloxypropyltris(trimethylsiloxy)silane and silicone methacrylamides, the hydrophobic vinyl monomers of formula (C) below:

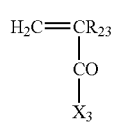

(C)

in which:

$R_{23}$ is chosen from H, —$CH_3$, —$C_2H_5$ and —$C_3H_7$ $X_3$ is chosen from:

alkyl ethers of —$OR_{24}$ type in which $R_{24}$ is a linear or branched, saturated or unsaturated hydrocarbon-based radical containing from 1 to 6 carbon atoms.

Mention is made, for example, of methyl methacrylate, ethyl methacrylate, n-butyl(meth)acrylate, tert-butyl(meth) acrylate, cyclohexyl acrylate and isobornyl acrylate and 2-ethylhexyl acrylate.

The water-soluble or water-dispersible AMPS polymers of the invention preferably have a molar mass ranging from 50 000 g/mol to 10 000 000 g/mol, preferably from 80 000 g/mol to 8 000 000 g/mol and even more preferably from 100 000 g/mol to 7 000 000 g/mol.

Examples of water-soluble or water-dispersible AMPS homopolymers in accordance with the invention that may be mentioned include crosslinked or non-crosslinked polymers of sodium acrylamido-2-methylpropanesulfonate, such as the polymer used in the commercial product Simulgel 800 (CTFA name: Sodium Polyacryloyldimethyltaurate).

Examples of water-soluble or water-dispersible AMPS copolymers in accordance with the invention that may be mentioned include:

acrylamide/sodium acrylamido-2-methylpropanesulfonate crosslinked copolymers, such as the copolymer used in the commercial product Sepigel 305 (CTFA name: Polyacrylamide/$C_{13}$-$C_{14}$ Isoparaffin/Laureth-7) or the copolymer used in the commercial product sold under the trade name Simulgel 600 (CTFA name: Acrylamide/Sodium Acryloyldimethyltaurate/Isohexadecane/Polysorbate-80) by the company SEPPIC;

copolymers of AMPS and of vinylpyrrolidone or of vinylformamide, such as the copolymer used in the commercial product sold under the name Aristoflex AVC by the company Clariant (CTFA name: Ammonium Acryloyldimethyltaurate/VP Copolymer) but neutralized with sodium hydroxide or potassium hydroxide;

copolymers of AMPS and of sodium acrylate, for instance AMPS/sodium acrylate copolymer such as the copolymer used in the commercial product sold under the name Simulgel EG by the company SEPPIC (CTFA name: Acrylamide/Sodium Acryloyldimethyltaurate/Isohexadecane/Polysorbate-80);

copolymers of AMPS and of hydroxyethyl acrylate, for instance AMPS/hydroxyethyl acrylate copolymer, such as the copolymer used in the commercial product sold under the name Simulgel NS by the company SEPPIC (CTFA name: Hydroxyethyl acrylate/Sodium Acryloyldimethyltaurate copolymer (and) Squalane (and) Polysorbate-60).

The preferred polymers are more particularly sodium acrylamido-2-methylpropanesulfonate homopolymers, such as the homopolymer used in the commercial product Sepigel 800, and AMPS/hydroxyethyl acrylate copolymers, such as the copolymer used in the commercial product sold under the name Simulgel NS.

According to one particularly preferred form of the invention, the AMPS polymer or copolymer will be used in powder form.

The aqueous phase gelling agents in accordance with the invention are generally present in active material amounts ranging from 0.01% to 20% by weight, more preferably from 0.1% to 10% by weight, even more preferably from 0.1% to 5% by weight and even more particularly from 0.5% to 2% by weight relative to the total weight of the gel.

The monocarbonyl or polycarbonyl self-tanning agents are chosen, for example, from isatin, alloxan, ninhydrin, glyceraldehyde, mesotartaric aldehyde, glutaraldehyde, erythrulose, pyrazoline-4,5-dione derivatives as described in patent application FR 2 466 492 and WO 97/35842, dihydroxyacetone (DHA) and 4,4-dihydroxypyrazolin-5-one derivatives as described in patent application EP-A-0 903 342.

In one particularly preferred embodiment of the invention, dihydroxyacetone (DHA) will be used as the self-tanning agent.

The self-tanning agents in accordance with the invention are generally present in the compositions in proportions ranging from 0.1% to 10% by weight relative to the total weight of the composition, and preferably from 0.2% to 8% by weight relative to the total weight of the composition.

The compositions in accordance with the invention may also contain other agents for artificially colouring the skin, among which mention may be made especially of indole derivatives, for instance monohydroxyindoles, as described in patent FR 2 651 126 (i.e.: 4-, 5-, 6- or 7-hydroxyindole) or dihydroxyindoles described in patent EP-B-0 425 324 (i.e.: 5,6-dihydroxyindole, 2-methyl-5,6-dihydroxyindole, 3-methyl-5,6-dihydroxyindole or 2,3-dimethyl-5,6-dihydroxyindole).

The aqueous self-tanning gels of the present invention may also employ at least one tinting agent. Examples of suitable tinting agents which may be used include, but are not limited to, red or orange dyes of the fluorane type, caramel, colored mica, colorless mica, pigments, titanium dioxide, and any other compound known to those skilled in the art, capable of imparting tint. The tinting agent will typically be present in the composition in an actives amount of from 0.0001 to 10.0% by weight, preferably from 0.001 to 5.0% by weight, and most preferably from 0.001 to 3.0% by weight, based on the weight of the composition.

The aqueous self-tanning gels of the present invention may also include at least one water-soluble or water-dispersible film-forming agent. For purposes of this invention, the term "water-soluble or water-dispersible" means that the substance in question will not precipitate out or coagulate, i.e., that it dissolves up to the limit of saturation.

Examples of suitable water-soluble or water-dispersible film-forming agents include, but are not limited to, hydrocolloids, for example: (a) water soluble non-gelling (at room temperature) natural polysaccharide or derivatives including pectin and derivatives, guar gum arabic, tragacanth gum, xanthan gum, gellan sodium salt, propyleneglycol alginate, starches (amylose, amylopectin), modified starches, hydroxyethyl starch, pullulan, carboxymethyl starch, gum ghatti, okra gum, karaya gum, dextrans, dextrins and maltodextrins, konjac, acemannan from aloe, locust bean gum, tara gum, quince seed gum, fenugreek seed gum, scleraglucan, gum arabic, psyllium seed gum, tamarind gum, oat gum, carrageenans, succinoglucan, larch arabinogalactan, flaxseed gum, chondroitin sulfates, hyaluronic acid, curdlan, chitosan, deacetylated konjac and rhizobium gum; (b) water soluble non-gelling polypeptide or protein exemplified by gelatins, albumins, milk proteins, soy protein and whey proteins; and, (c) synthetic hydrocolloids exemplified by polyethyleneimine, hydroxyethyl cellulose, sodium carboxymethyl cellulose, carboxymethyl cellulose, hydroxypropyl cellulose, sodium carboxymethyl cellulose, methyl cellulose, ethyl cellulose, polyacrylic acids, low molecular weight polyacrylamides and their sodium salts (carbomers), polyvinylpyrollidone, polyethylene glycols, polyethylene oxides, polyvinyl alcohols, pluronics, tetronics, and other block co-polymers, carboxyvinyl polymers, and colloidal silicon dioxide.

Additional examples of water-soluble or water-dispersible film-forming agents include, but are by no means limited to, polymers formed from monomers selected from the group consisting of olefin oxides, vinyl pyrrolidone, vinyl esters, vinyl alcohols, vinyl cyanides, oxazilines, carboxylic acids and esters and mixtures thereof. Preferred vinyl pyrrolidone polymers are selected from the group consisting of polyvinylpyrrolidone, vinyl acetate/vinyl pyrrolidone copolymer and mixtures thereof. Preferred polyvinyl esters are selected form the group consisting of vinyl acetate/crotonic acid copolymer, vinyl acetate/crotonic acid/vinyl neodecanoate copolymer and mixtures thereof. Preferred vinyl alcohol polymers are selected from the group consisting of vinyl alcohol/vinyl acetate, vinyl alcohol/poly(alkyleneoxy)acrylate, vinyl alcohol/vinyl acetate/poly-(alkyleneoxy)acrylate and mixtures thereof. Preferred olefin oxides are selected from the group consisting of polyethylene oxide, polypropylene oxide and mixtures thereof. Preferred polycarboxylic acids and their esters are selected from the group consisting of acrylates, acrylates/octylacrylamide copolymers and mixtures thereof. The preferred oxazilines is polyoxazilines.

Specific water-soluble or water-dispersible film-forming agents useful in the present invention include, but are not necessarily limited to Polyox WSR (polyethyleneoxide polymers) from Union Carbide; Airvol (polyvinylalcohol copolymer) from Air Products and Chemicals, preferably all commercially available grades like Airvol 103, Airvol 325, Airvol 540, Airvol 523S; Vinex from Air Products and Chemicals, preferably all commercially available grades such as Vinex 1003, Vinex 2034, Vinex 2144, Vinex 2019; PEOX. (polyethyloxazoline) from Polymer Chemistry Innovations; PVP K Series (polyvinylpyrrolidone) from International Specialty Products; Luviskol K Series (polyvinylpyrrolidone) from BASF; PVP/VA (vinyl acetate/vinyl pyrrolidone copolymer) from International Specialty Products, preferably grades W-735 and S-630; and Gantrez (copolymers of methyl vinyl ether/maleic anhydride) from International Specialty Products; Polymer EX33-9 available from Interpolymer (acrylate copolymer); Carboset Series (acrylate copolymer) from BF Goodrich; Resyn Series (vinyl acetate/crotonate copolymers) from National Starch and Chemical Corporation; Versatyl and Dermacryl Series (acrylate/octylacrylamide copolymers) from National Starch and Chemical Corporation.

The water-soluble or water-dispersible film-forming agent may be present in an amount of from 0.01 to 20.0% by weight, preferably from 0.1 to 10.0% by weight, and more preferably from 0.1 to 5.0% by weight, based on the weight of the composition.

The present invention may also additionally contain at least one UVA-active and/or UVB-active organic UV-screening agent; the said UV-screening agent may be water-soluble, liposoluble or insoluble in the cosmetic solvents commonly used.

The organic screening agents are chosen especially from anthranilates; cinnamic derivatives; dibenzoylmethane derivatives; salicylic derivatives; camphor derivatives; triazine derivatives such as those described in patent applications U.S. Pat. No. 4,367,390, EP 863 145, EP 517 104, EP 570 838, EP 796 851, EP 775 698, EP 878 469, EP 933 376, EP 507 691, EP 507 692, EP 790 243, EP 944 624, the entire contents of which are hereby incorporated by reference; benzophenone derivatives; $\beta,\beta$-diphenylacrylate derivatives; benzotriazole derivatives; benzalmalonate derivatives; benzimidazole derivatives; imidazolines; bis-benzazolyl derivatives as described in patents EP 669 323 and U.S. Pat. No. 2,463,264, the entire contents of which are hereby incorporated by reference; p-aminobenzoic acid (PABA) derivatives; benzoxazole derivatives as described in patent applications EP 0 832 642, EP 1 027 883, EP 1 300 137 and DE 101 62 844, the entire contents of which are hereby incorporated by reference; methylenebis(hydroxyphenylbenzotriazole) derivatives as described in patent applications U.S. Pat. No. 5,237,071, U.S. Pat. No. 5,166,355, GB 2 303 549, DE 197 26 184 and EP 893 119, the entire contents of which are hereby incorporated by reference; screening polymers and screening silicones such as those described especially in patent application WO 93/04665, the entire content of which is hereby incorporated by reference; dimers derived from $\alpha$-alkylstyrene, such as those described in patent application DE 198 55 649, the entire content of which is hereby incorporated by reference; 4,4-diarylbutadienes such as those described in patent applications DE 197 55 649, EP 916 335, EP 1 133 980 and EP 1 133 981 and EP-A-1 008 586, the entire contents of which are hereby incorporated by reference, and mixtures thereof.

As examples of UV-A-active and/or UV-B-active organic screening agents, mention may be made of those denoted hereinbelow under their INCI name:

para-Aminobenzoic Acid Derivatives:
  PABA,
  Ethyl PABA,
  Ethyl dihydroxypropyl PABA,
  Ethylhexyl dimethyl PABA sold in particular under the name "Escalol 507" by ISP,
  Glyceryl PABA,
  PEG-25 PABA sold under the name "Uvinul P25" by BASF.

Salicylic Derivatives:
Homosalate sold under the name "Eusolex HMS" by Rona/EM Industries,
Ethylhexyl salicylate sold under the name "Neo Heliopan OS" by Haarmann and Reimer,
Dipropylene glycol salicylate sold under the name "Dipsal" by Scher,
TEA salicylate sold under the name "Neo Heliopan TS" by Haarmann and Reimer.

Dibenzoylmethane Derivatives:
Butyl methoxydibenzoylmethane sold in particular under the trade name "Parsol 1789" by Hoffmann LaRoche,
Isopropyldibenzoylmethane.

Cinnamic Derivatives:
Ethylhexyl methoxycinnamate sold in particular under the trade name "Parsol MCX" by Hoffmann LaRoche,
Isopropyl methoxycinnamate,
Isoamyl methoxycinnamate sold under the trade name "Neo Heliopan E 1000" by Haarmann and Reimer,
Cinoxate,
DEA methoxycinnamate,
Diisopropyl methylcinnamate,
Glyceryl ethylhexanoate dimethoxycinnamate.

$\beta,\beta$-Diphenylacrylate Derivatives:
octocrylene sold in particular under the trade name "Uvinul N539" by BASF,
Etocrylene sold in particular under the trade name "Uvinul N35" by BASF.

Benzophenone Derivatives:
Benzophenone-1 sold under the trade name "Uvinul 400" by BASF,
Benzophenone-2 sold under the trade name "Uvinul D50" by BASF,
Benzophenone-3 or Oxybenzone sold under the trade name "Uvinul M40" by BASF,
Benzophenone-4 sold under the trade name "Uvinul MS40" by BASF,
Benzophenone-5,
Benzophenone-6 sold under the trade name "Helisorb 11" by Norquay,
Benzophenone-8 sold under the trade name "Spectra-Sorb UV-24" by American Cyanamid,
Benzophenone-9 sold under the trade name "Uvinul DS-49" by BASF,
Benzophenone-12,
n-Hexyl 2-(4-diethylamino-2-hydroxybenzoyl)benzoate.

Benzylidenecamphor Derivatives:
3-Benzylidenecamphor manufactured under the name—"Mexoryl SD" by Chimex,
4-Methylbenzylidenecamphor sold under the name—"Eusolex 6300" by Merck,
Benzylidenecamphorsulfonic acid manufactured under the name "Mexoryl SL" by Chimex,
Camphor benzalkonium methosulfate manufactured under the name "Mexoryl SO" by Chimex,
Terephthalylidenedicamphorsulfonic acid manufactured under the name "Mexoryl SX" by Chimex,
Polyacrylamidomethylbenzylidenecamphor manufactured under the name "Mexoryl SW" by Chimex.

Phenylbenzimidazole Derivatives:
Phenylbenzimidazolesulfonic acid sold in particular under the trade name "Eusolex 232" by Merck,
Benzimidazilate sold under the trade name "Neo Heliopan AP" by Haarmann and Reimer.

Triazine Derivatives:
Anisotriazine sold under the trade name "Tinosorb S" by Ciba Geigy,
Ethylhexyltriazone sold in particular under the trade name "Uvinul T150" by BASF,
Diethylhexylbutamidotriazone sold under the trade name "Uvasorb HEB" by Sigma 3V,
2,4,6-Tris(diisobutyl 4'-aminobenzalmalonate)-s-triazine.

Phenylbenzotriazole Derivatives:
Drometrizole trisiloxane sold under the name "Silatrizole" by Rhodia Chimie,
Methylenebis(benzotriazolyl)tetramethylbutylphenol sold in solid form under the trade name "Mixxim BB/100" by Fairmount Chemical, or in micronized form as an aqueous dispersion under the trade name "Tinosorb M" by Ciba Specialty Chemicals.

Anthranilic Derivatives:
Menthyl anthranilate sold under the trade name "Neo Heliopan MA" by Haarmann and Reimer.

Imidazoline Derivatives:
Ethylhexyldimethoxybenzylidenedioxoimidazoline propionate.

Benzalmalonate Derivatives:
Polyorganosiloxane containing benzalmalonate functions sold under the trade name "Parsol SLX" by Hoffmann La Roche.

4,4-Diarylbutadiene Derivatives:
1,1-Dicarboxy(2',2'-dimethylpropyl)-4,4-diphenylbutadiene.

Benzoxazole Derivatives:
2,4-Bis[5-1(dimethylpropyl)benzoxazol-2-yl(4-phenyl)imino]-6-(2-ethylhexyl)imino-1,3,5-triazine sold under the name Uvasorb K2A by Sigma 3V,
and mixtures thereof.

The organic UV-screening agents that are more particularly preferred are chosen from the following compounds:
Ethylhexyl salicylate,
Butyl methoxydibenzoylmethane,
Ethylhexyl methoxycinnamate,
Octocrylene,
Phenylbenzimidazolesulfonic acid,
Terephthalylidenedicamphorsulfonic acid,
Benzophenone-3,
Benzophenone-4,
Benzophenone-5,
n-Hexyl 2-(4-diethylamino-2-hydroxybenzoyl)benzoate,
4-Methylbenzylidenecamphor,
Benzimidazilate,
Anisotriazine,
Ethylhexyltriazone,
Diethylhexylbutamidotriazone,
2,4,6-Tris(diisobutyl 4'-aminobenzalmalonate)-s-triazine,
Methylenebis(benzotriazolyl)tetramethylbutylphenol,
Drometrizole trisiloxane,
Polysilicone-15
1,1-Dicarboxy(2',2'-dimethylpropyl)-4,4-diphenylbutadiene,
2,4-Bis[5-1(dimethylpropyl)benzoxazol-2-yl(4-phenyl)imino]-6-(2-ethylhexyl)imino-1,3,5-triazine
and mixtures thereof.

The UV-screening agents in accordance with the invention are generally present in the gels according to the invention in proportions ranging from 0.1 to 20% by weight and preferably ranging from 0.2% to 15% by weight relative to the total weight of the gel.

The gels in accordance with the present invention may also comprise standard cosmetic adjuvants chosen especially from fatty substances, organic solvents, ionic or nonionic thickeners, softeners, antioxidants, free-radical scavengers, stabilizers, sequestering agents, emollients, silicones, α-hydroxy acids, antifoams, moisturizers, vitamins, insect repellents, fragrances, preserving agents, surfactants, anti-inflammatory agents, substance P antagonists, fillers, polymers, propellants, acidifying or basifying agents, or any other ingredient usually used in cosmetics and/or dermatology.

The fatty substances may consist of an oil or mixtures of oils. The term "oil" means a compound that is liquid at room temperature.

Oils that may be mentioned include mineral oils (paraffin); plant oils (sweet almond oil, macadamia oil, blackcurrant seed oil or jojoba oil); synthetic oils, for instance perhydrosqualene, fatty alcohols, fatty acids or fatty esters (for instance the $C_{12}$-$C_{15}$ alkyl benzoate sold under the trade name "Finsolv TN" by the company Finetex, octyl palmitate, isopropyl lanolate, triglycerides, including capric/caprylic acid triglycerides), oxyethylenated or oxypropylenated fatty esters and ethers; silicone oils (cyclomethicone, polydimethylsiloxanes or PDMS) or fluoro oils, and polyalkylenes.

The aqueous phase of the said compositions contains water and, in general, other water-soluble or water-miscible solvents. The water-soluble or water-miscible solvents comprise short-chain monoalcohols, for example of $C_1$-$C_4$, for instance ethanol or isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, and sorbitol. Propylene glycol and glycerol will be used more particularly.

Needless to say, a person skilled in the art will take care to select the optional additional compound(s) mentioned above and/or the amounts thereof such that the advantageous properties intrinsically associated with the invention are not, or are not substantially, adversely affected by the envisaged addition(s).

The present invention also relates to a process for making a transfer resistant and stable self-tanning aqueous gel composition, involving the steps of:
a) providing a cosmetically acceptable support;
b) providing at least one monocarbonyl or polycarbonyl self-tanning agent;
c) providing an aqueous-phase gelling agent comprised of at least one water-soluble or water-dispersible, crosslinked or non-crosslinked polymer or copolymer;
d) optionally, providing at least one tinting agent;
e) optionally, providing at least one water-soluble or water-dispersible film-forming agent; and
f) combining (a)-(e) to form a transfer resistant and stable self-tanning aqueous gel composition.

The invention also relates to a cosmetic treatment process for artificially tanning and/or browning the skin involving contacting the skin with an effective amount of a composition as defined above.

Concrete, but in no way limiting, examples illustrating the invention will now be given.

EXAMPLES

Example: Tinted Self-Tanning Gel in Accordance W/Present Invention

| FORMULA: BATCH #: | | total %: | 100.000 | bal %: | 0.000 | BATCH WT: | 1,000 |
|---|---|---|---|---|---|---|---|
| Phase | INCI/Chemical Name | | % wt/wt | | g/1000 g | Lot # | |
| A | Water | | 66.289 | | 662.89 | | |
| | Red # 33 | | 0.0006 | | 0.006 | | |
| | Yellow # 6 | | 0.010 | | 0.10 | | |
| | Methyl Paraben | | 0.200 | | 2.00 | | |
| | Hydroxyethyl Acrylate/Sodium Acryloyldimethyl Taurate Copolymer | | 1.700 | | 17.00 | | |
| B | Caramel | | 1.000 | | 10.00 | | |
| | Water | | 5.000 | | 50.00 | | |
| C | Fragrance | | 0.300 | | 3.00 | | |
| | PPG-26 Buteth-26 (and) PEG-40 Hydrogenated Castor oil | | 0.300 | | 3.00 | | |
| | Tocopherol (and) Glycine Soja (soybean) Oil | | 0.100 | | 1.00 | | |
| D | Water | | 10.000 | | 100.00 | | |
| | DHA | | 7.000 | | 70.00 | | |
| E | Synthetic Fluorphlogopite | | 0.100 | | 1.00 | | |
| F | VP/VA Copolymer | | 1.000 | | 10.00 | | |
| G | Ethanol | | 7.000 | | 70.00 | | |

Comparative Example

In the comparative example, Hydroxyethyl Acrylate/Sodium Acryloyldimethyl Taurate Copolymer was replaced with Polyquaternium-10.

| FORMULA: BATCH #: | | total %: | 100.000 | bal %: | 0.000 | BATCH WT: | 1,000 |
|---|---|---|---|---|---|---|---|
| Phase | INCI/Chemical Name | | % wt/wt | | g/1000 g | Lot # | |
| A | Water | | 66.289 | | 662.89 | | |
| | Red # 33 | | 0.0006 | | 0.006 | | |
| | Yellow # 6 | | 0.010 | | 0.10 | | |
| | Methyl Paraben | | 0.200 | | 2.00 | | |
| | Polyquaternium-10 | | 1.700 | | 17.00 | | |
| B | Caramel | | 1.000 | | 10.00 | | |
| | Water | | 5.000 | | 50.00 | | |
| C | Fragrance | | 0.300 | | 3.00 | | |
| | PPG-26 Buteth-26 (and) PEG-40 Hydrogenated Castor oil | | 0.300 | | 3.00 | | |
| | Tocopherol (and) Glycine Soja (soybean) Oil | | 0.100 | | 1.00 | | |
| D | Water | | 10.000 | | 100.00 | | |
| | DHA | | 7.000 | | 70.00 | | |
| E | Synthetic Fluorphlogopite | | 0.100 | | 1.00 | | |
| G | Ethanol | | 7.000 | | 70.00 | | |

In house testing of the two formulations revealed that the comparative example yielded undesirable peeling.

What is claimed is:

1. A self-tanning aqueous gel composition comprising:
   (a) a cosmetically acceptable support;
   (b) at least one monocarbonyl or polycarbonyl self-tanning agent;
   (c) at least one aqueous phase gelling agent comprised of at least one water-soluble or water-dispersible, crosslinked or non-crosslinked polymer or copolymer selected from the group consisting of i) sodium polyacryloyldimethyltaurate; ii) a copolymer of acrylamido-2-methylpropanesulfonic acid (AMPS) and sodium acrylate; and iii) a copolymer of acrylamido 2-methylpropanesulfonic acid (AMPS) and hydroxyethyl acrylate; wherein the polymer or copolymer is partially or completely neutralized with a mineral base other than ammonia;
   (d) at least one tinting agent; and
   (e) at least one water-soluble or water-dispersible film-forming agent,
wherein the composition is in the form of an aqueous gel comprising a continuous aqueous phase containing a viscoelastic mass formed from colloidal suspensions.

2. The composition of claim 1 wherein the aqueous phase is present in an amount of at least about 70% by weight, based on the total weight of the composition.

3. The composition of claim 1 wherein the at least one water-soluble or water-dispersible, crosslinked or non-crosslinked polymer or copolymer in (c) is sodium polyacryloyldimethyltaurate, in a form partially or totally neutralized with sodium hydroxide.

4. The composition of claim 1 wherein the at least one water-soluble or water-dispersible, crosslinked or non-crosslinked polymer or copolymer in (c) is a copolymer of acrylamido-2-methylpropanesulfonic acid (AMPS) and sodium acrylate or a copolymer of acrylamido 2-methylpropanesulfonic acid (AMPS) and hydroxyethyl acrylate.

5. The composition of claim 1 wherein (c) is present in an amount of from about 0.01% to about 20% by weight, based on the weight of the composition.

6. The composition of claim 1 wherein (b) is dihydroxyacetone (DHA).

7. The composition of claim 1 wherein (b) is present in an amount of from about 0.1% to about 10% by weight, based on the weight of the composition.

8. The composition of claim 1 wherein (d) is present in the composition in an amount of from about 0.00001 to about 10.0% by weight, based on the weight of the composition.

9. The composition of claim 1 wherein (e) is a vinyl pyrrolidone/vinyl acetate copolymer.

10. The composition of claim 1 wherein (e) is present in the composition in an amount of from about 0.01 to about 20.0% by weight, based on the weight of the composition.

11. The composition of claim 1 further comprising at least one UV-screening agent chosen from UVA-active organic UV-screening agents and UVB-active organic UV-screening agents.

12. The composition of claim 11 wherein the UV-screening agent is present in the composition in an amount of from about 0.1% to about 20% by weight, based on the weight of the composition.

13. A process for making a transfer resistant and stable self-tanning aqueous gel composition comprising:
  (a) providing a cosmetically acceptable support;
  (b) providing at least one monocarbonyl or polycarbonyl self-tanning agent;
  (c) providing at least one aqueous phase gelling agent comprised of at least one water-soluble or water-dispersible, crosslinked or non-crosslinked polymer or copolymer selected from the group consisting of i) sodium polyacryloyldimethyltaurate; ii) a copolymer of acrylamido-2-methylpropanesulfonic acid (AMPS) and sodium acrylate; and iii) a copolymer of acrylamido 2-methylpropanesulfonic acid (AMPS) and hydroxyethyl acrylate; wherein the polymer or copolymer is partially or completely neutralized with a mineral base other than ammonia;
  (d) optionally, providing at least one tinting agent;
  (e) providing at least one water-soluble or water-dispersible film-forming agent; and
  (f) combining (a)-(e) to form a transfer resistant and stable self-tanning aqueous gel composition comprising a continuous aqueous phase containing a viscoelastic mass formed from colloidal suspensions.

14. The process of claim 13 wherein the aqueous phase is present in an amount of at least about 70% by weight, based on the total weight of the composition.

15. The process of claim 13 wherein the at least one water-soluble or water-dispersible, crosslinked or non-crosslinked polymer or copolymer in (c) is sodium polyacryloyldimethyltaurate, in a form partially or totally neutralized with sodium hydroxide.

16. The process of claim 13 wherein the at least one water-soluble or water-dispersible, crosslinked or non-crosslinked polymer or copolymer in (c) is a copolymer of acrylamido-2-methylpropanesulfonic acid (AMPS) and sodium acrylate or a copolymer of acrylamido 2-methylpropanesulfonic acid (AMPS) and hydroxyethyl acrylate.

17. The process of claim 13 wherein (c) is present in an amount of from about 0.01% to about 20% by weight, based on the weight of the composition.

18. The process of claim 13 wherein (b) is dihydroxyacetone (DHA).

19. The process of claim 13 wherein (b) is present in an amount of from about 0.1% to about 10% by weight, based on the weight of the composition.

20. The process of claim 13 wherein (d) is present in the composition in an amount of from about 0.00001 to about 10.0% by weight, based on the weight of the composition.

21. The process of claim 12 wherein (e) is a vinyl pyrrolidone/vinyl acetate copolymer.

22. The process of claim 13 wherein (e) is present in the composition in an amount of from about 0.01 to about 20.0% by weight, based on the weight of the composition.

23. The process of claim 13 further comprising at least one UV-screening agent chosen from UVA-active organic UV-screening agents and UVB-active organic UV-screening agents.

24. The process of claim 23 wherein the UV-screening agent is present in the composition in an amount of from about 0.1% to about 20% by weight, based on the weight of the composition.

25. A process for artificially tanning and/or browning human skin in a transfer resistant manner comprising contacting the skin with the composition of claim 1.

* * * * *